US009999378B2

United States Patent
Ronchi et al.

(10) Patent No.: US 9,999,378 B2
(45) Date of Patent: Jun. 19, 2018

(54) METHOD AND APPARATUS FOR MONITORING DEVIATION OF A LIMB

(71) Applicant: DORSAVI LTD, Victoria (AU)

(72) Inventors: Daniel M. Ronchi, Victoria (AU);
Andrew J. Ronchi, Victoria (AU);
Edgar Charry, Victoria (AU);
Wenzheng Hu, Victoria (AU)

(73) Assignee: DORSAVI LTD, Melbourne East (AU)

( * ) Notice: Subject to any disclaimer, the term of this patent is extended or adjusted under 35 U.S.C. 154(b) by 78 days.

(21) Appl. No.: 14/441,809

(22) PCT Filed: Nov. 8, 2013

(86) PCT No.: PCT/AU2013/001295
§ 371 (c)(1),
(2) Date: May 8, 2015

(87) PCT Pub. No.: WO2014/071460
PCT Pub. Date: May 15, 2014

(65) Prior Publication Data
US 2015/0272484 A1    Oct. 1, 2015

(30) Foreign Application Priority Data
Nov. 9, 2012    (AU) ................................ 2012904946

(51) Int. Cl.
*A61B 5/00* (2006.01)
*A61B 5/11* (2006.01)

(52) U.S. Cl.
CPC ........... *A61B 5/1122* (2013.01); *A61B 5/1114* (2013.01); *A61B 5/1123* (2013.01);
(Continued)

(58) Field of Classification Search
CPC ....... A61B 5/11; A61B 5/1114; A61B 5/1116; A61B 5/1121–5/23; A61B 5/4571; A61B 5/4585; A61B 5/4595; A61B 5/7253
See application file for complete search history.

(56) References Cited

U.S. PATENT DOCUMENTS 5,615,132 A    3/1997 Horton et al.
9,597,015 B2 *    3/2017 McNames ............ A61B 5/1071
(Continued)

FOREIGN PATENT DOCUMENTS

CN    1689513 A    11/2005
CN    102579051 A    7/2012
(Continued)

OTHER PUBLICATIONS

European Search Report and Written Opinion issued in counterpart European Application No. EP 13853301.3, dated May 25, 2016. 7 pages.
(Continued)

*Primary Examiner* — Max Hindenburg
(74) *Attorney, Agent, or Firm* — Mintz Levin Cohn Ferris Glovsky and Popeo, P.C.; Michael D. Van Loy

(57) ABSTRACT

Apparatus is disclosed for monitoring, measuring and/or estimating deviation of a body part of a vertebral mammal. The apparatus includes at least one sensor for measuring rotation of the body part relative to a first frame of reference and for providing data indicative of the rotation. The apparatus also includes a memory device adapted for storing the data and a processor adapted for processing the data to evaluate a deviation of the body part that correlates to the data. The processor may be configured to execute an algorithm for evaluating deviation of the body part. A method of monitoring, measuring and/or estimating deviation of a body part of a vertebral mammal is also disclosed.

28 Claims, 3 Drawing Sheets

(52) U.S. Cl.
CPC .......... *A61B 5/4571* (2013.01); *A61B 5/4585* (2013.01); *A61B 5/4595* (2013.01); *A61B 5/7253* (2013.01); *A61B 2560/0475* (2013.01); *A61B 2562/0219* (2013.01)

(56) References Cited

U.S. PATENT DOCUMENTS

| | | |
|---|---|---|
| 2009/0088674 A1 | 4/2009 | Caillouette et al. |
| 2010/0063508 A1 | 3/2010 | Borja et al. |
| 2011/0028865 A1 | 2/2011 | Luinge et al. |
| 2011/0213275 A1 | 9/2011 | Boos et al. |
| 2011/0270132 A1 | 11/2011 | Mezghani et al. |
| 2011/0306903 A1 | 12/2011 | Crabtree et al. |

FOREIGN PATENT DOCUMENTS

| | | |
|---|---|---|
| EP | 0710466 A1 | 5/1996 |
| WO | WO-2005/104945 A2 | 11/2005 |

OTHER PUBLICATIONS

Patent Examination Report No. 1 issued in counterpart Australian Application No. 2013344326, dated Jul. 17, 2017. 4 pages.

The State Intellectual Property Office, P.R. China First Office Action and Search Report issued in counterpart Chinese Patent Application No. 201380058811.0, dated Oct. 9, 2016. [Chinese language]. 11 pages.

The State Intellectual Property Office, P.R. China First Office Action and Search Report issued in counterpart Chinese Patent Application No. 201380058811.0, dated Oct. 9, 2016. [English language translation]. 15 pages.

The State Intellectual Property Office, P.R. China Second Office Action and Search Report issued in counterpart Chinese Patent Application No. 201380058811.0, dated Jul. 28, 2017 [Chinese language]. 7 pages.

The State Intellectual Property Office, P.R. China Second Office Action and Search Report issued in counterpart Chinese Patent Application No. 201380058811.0, dated Jul. 28, 2017. [English language translation]. 11 pages.

* cited by examiner

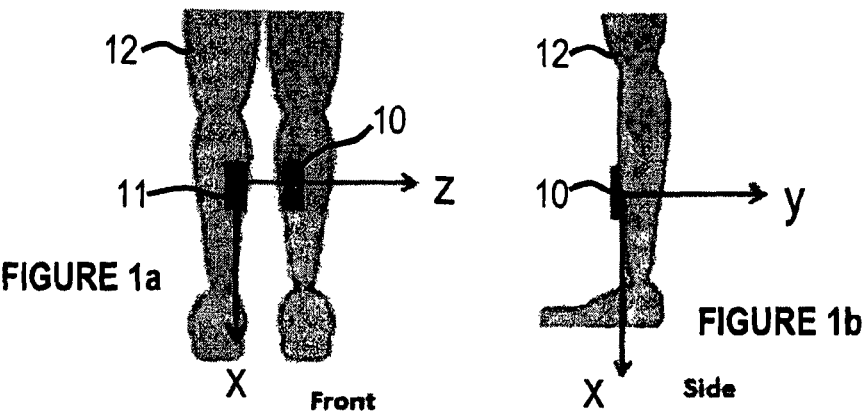
FIGURE 1a
FIGURE 1b
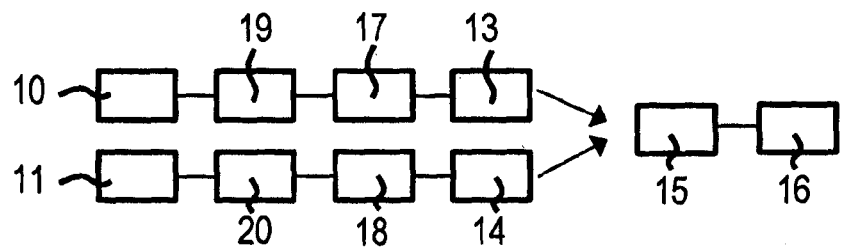
FIGURE 1c
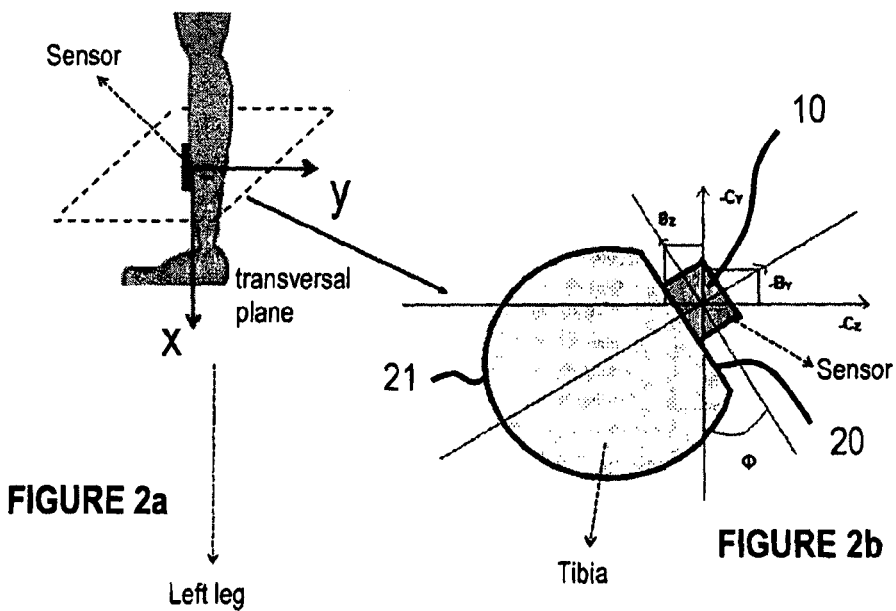
FIGURE 2a
FIGURE 2b

METHOD AND APPARATUS FOR MONITORING DEVIATION OF A LIMB

CROSS REFERENCE TO RELATED APPLICATIONS

The current application is a national-phase entry of Patent Cooperation Treaty application no. PCT/AU2013/001295, which has an international filing date of Nov. 8, 2013, and which claims the priority of Australian patent application no. 2012904946, filed on Nov. 9, 2012. The specifications, claims, and figures of both the PCT and Australian applications are incorporated herein by reference in their entireties.

FIELD OF THE INVENTION

The present invention relates to a method and apparatus for monitoring, measuring, estimating and/or providing feedback on deviation of a body part of a vertebral mammal such as medio-lateral deviation, also known as a change in lower extremity angular alignment. Medio-lateral deviation may manifest during activities and/or movements such as squatting, hopping and/or running.

BACKGROUND OF THE INVENTION

Knee injuries are common and are painful events for recreational and elite sportspersons. A well-documented risk factor for knee injuries is the degree of change in angular alignment occurring at the knee joint during a dynamic activity. The change in angular alignment is commonly referred to as valgus or varus depending on whether the knee angles inward (valgus) or outwards (varus). In anatomical terms, alignment of the tibial tubercle with the pelvis is also referred to as Q-angle. The change in angular alignment of the knee describes the knee moving medially whilst the foot is fixed to the ground (valgus) or the knee moving laterally whilst the foot is fixed to the ground (varus), increasing the angle between the femur and the tibia. When movement causing change in angular alignment of the knee occurs, it may be in combination with flexion of the knee known as tibio-femoral flexion, internal rotation of the femur, pronation of the foot and/or relative flexion of the hip joint.

Alignment of the knee, hip and ankle as a person squats, jumps, hops, walks or runs has been a regular test or assessment carried out by therapists when assessing an athlete or sportsperson. The therapist may subjectively (visually) rate whether the athlete/sportsperson performed the test well or poorly using a rating system such as 1 (good), 2 (average) or 3 (poor).

Although the rating system may provide a subjective impression of valgus or varus movement when squatting or landing from a hop/jump, the test is currently not measured objectively and instead is subjectively assessed based on visual observations. Video techniques may be used to visualise alignment of the femur with the tibia, while software packages may allow a user to align traces on a screen with angular motion of different limbs of the body to estimate the valgus/varus angle. Optical tracking markers may also be used with high frame rate cameras to capture this type of movement in a laboratory setting. However, these procedures are time consuming to post analyse, often have visual occlusions due to limb movement, do not provide real time data and typically need to be captured in a controlled environment with access to specialist equipment and staff.

The method and apparatus of the present invention may at least alleviate the disadvantages of the prior art. The present invention may also provide real time feedback, while not requiring video analysis, to allow an athlete/player to adjust their movement patterns in real time, based on the real time feedback.

A reference herein to a patent document or other matter which is given as prior art is not to be taken as an admission that that document or matter was known or that the information it contains was part of the common general knowledge in Australia or elsewhere as at the priority date of any of the disclosure or claims herein. Such discussion of prior art in this specification is included to explain the context of the present invention in terms of the inventor's knowledge and experience.

Throughout the description and claims of this specification the words "comprise" or "include" and variations of those words, such as "comprises", "includes" and "comprising" or "including, are not intended to exclude other additives, components, integers or steps.

SUMMARY OF THE INVENTION

According to one aspect of the present invention there is provided apparatus for monitoring, measuring, and/or estimating deviation of a body part of a vertebral mammal, said apparatus including:

at least one sensor for measuring rotation of said body part relative to a frame of reference and for providing data indicative of said rotation;

a memory device adapted for storing said data; and a processor adapted for processing said data to evaluate a deviation of said body part that correlates to said data.

The processor may be configured to execute an algorithm for evaluating deviation of the body part. The algorithm may be adapted to transform data from the first frame of reference relative to a second frame of reference in which the body part performs a movement.

The algorithm may be adapted to integrate the data over a period of time to provide an angular displacement ($\theta$). The algorithm may be adapted to evaluate a component ($\theta_Z$) of the angular displacement representing angular displacement such as valgus or varus angle. The algorithm may be adapted to project the lateral flexion component ($\theta_Z$) onto a frontal plane.

The algorithm may be adapted to evaluate a twist component ($\theta_X$) of the angular displacement representing twist angle. The algorithm may be adapted to compensate the twist component ($\theta_X$) by adding an angular offset ($\theta_{x0}$) to the twist component ($\theta_X$). The angular offset ($\theta_{x0}$) caused by components $\theta_Y$ and $\theta_Z$ of the angular displacement may be determined by $\theta_{x0} = a\tan(\sin(\theta_Z)/\tan(\theta_Y))$.

The at least one sensor may include a gyroscope. The at least one sensor may be adapted for measuring rotation around one or more orthogonal axes. The at least one sensor may further include means for measuring acceleration of the body part relative to an inertial frame of reference and for providing data indicative of the acceleration. The acceleration means may be adapted for measuring acceleration along one or more orthogonal axes.

The body part of the mammal may include legs and the apparatus may be adapted to monitor rotation components associated with the legs. Respective sensors may be applied to legs of the mammal. The or each sensor may include an analog to digital (A to D) converter for converting analog data to a digital domain. The A to D converter may be configured to convert an analog output from the or each sensor to the data prior to storing the data. Capturing angular deviation during dynamic lower extremity movements may require a sampling frequency that is at least sufficient and commensurate with frequency of the movement(s).

According to a further aspect of the present invention there is provided a method of monitoring, measuring, and/or estimating deviation of a body part of a vertebral mammal, said method including:

using at least one sensor to measure rotation of said body part relative to a frame of reference and for providing data indicative of said rotation;

storing said data in a memory device; and processing said data by a processor to evaluate a deviation of said body part that correlates to said data.

DESCRIPTION OF THE DRAWINGS

FIG. 1 shows one form of apparatus according to the present invention;

FIG. 2 shows a cross-sectional view in the transversal plane of the left leg and sensor placed on the tibia;

DESCRIPTION OF A PREFERRED EMBODIMENT

Figure 3:
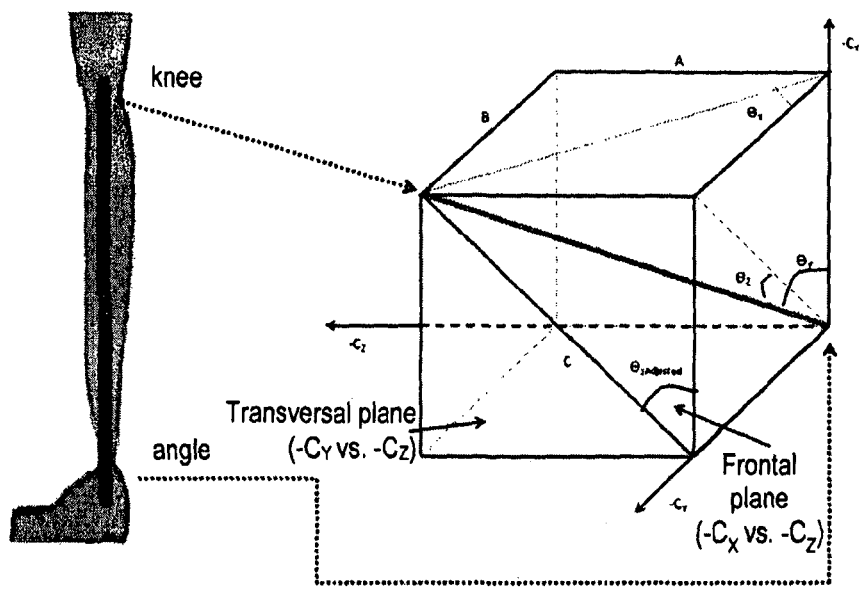
FIG. 3 shows a projection of the $\theta_Z$ plane onto the frontal plane with twist update.

The present invention is particularly suitable for monitoring and ascertaining medio/lateral deviation of the knee of a human subject at a given point in time and is described herein in this context. Nevertheless, it is to be understood that the present invention is not thereby limited to such applications.

The present invention may monitor medio-lateral deviation of the knee in a variety of environments including indoor and/or outdoor environments and for diverse purposes including but not limited to applications such as monitoring and measuring medio/lateral deviation of the knee experienced by athletes in order to identify poor control, prevent injuries, identify lack of muscular control and/or inflexibility, guide adoption of optimal technique, confirm completion of recovery (for injured athletes) and/or improve overall performance.

The apparatus of the present invention may be placed on the medial part of the shank of a leg to enable monitoring of medio-lateral deviation, also known as valgus/varus of the knee, during squatting, jumping, hopping, walking and/or running. The apparatus may include rotation sensors such as gyroscopes and optionally one or more inertial sensors such as accelerometers and/or magnetometers to ascertain medio-lateral deviation. The apparatus may include a digital processing engine configured to execute one or more algorithms. The algorithm(s) may take account of variables such as angle of the tibia with respect to the transverse plane and/or twisting of the leg during an activity.

Referring to FIG. 1, one form of apparatus according to the present invention includes sensors 10, 11 placed along or in-line with tibial axes of the left and right legs of a human subject 12. Sensors 10, 11 are placed on the legs of subject 12 such that the frames of reference of sensors 10, 11 are defined by axes x,y,z with axes x,z being in the plane of FIG. 1 (front view) and axes x,y being in the plane of FIG. 1 (side view). Measurement of Valgus or Varus is defined as rotation around the y axis.

Each sensor 10, 11 may include a rotation sensor such as a 1D, 2D or 3D gyroscope to measure angular velocity and optionally a 1D, 2D or 3D accelerometer to measure acceleration and/or a magnetic sensor such as a magnetometer to measure magnetic field. The positive axes on both legs may point up or down so that tibial acceleration may be measured in a vertical direction at least. Data from sensors 10, 11 may be used to ascertain medio-lateral deviation of the legs of subject 12 during activities and/or movements such as squatting, hopping and/or running.

Sensor data measured via sensors 10, 11 may be sent via wireless transmitters 13, 14 to remote receiver 15. Receiver 15 is associated with digital processing engine 16. Digital processing engine 16 includes a digital processor such as a microprocessor for processing data.

Digital processing engine 16 may include an algorithm for ascertaining medio-lateral deviation of the knees using angular velocities and accelerations measured from the antero medial aspect of each tibia. Digital processing engine 16 may perform calculations with the algorithm following transformation of data from the frame of reference of each sensor 10, 11 to the frame of reference of the mechanical axis of each tibia.

In one form a digital memory or data storing means 17, 18, may be associated with sensors 10, 11 for storing data in digital format for analysis and/or reporting. Digital memory 17, 18 may include structure such as flash memory, memory card, memory stick or the like for storing digital data. The memory structure may be removable to facilitate downloading the data to a remote processing device such as a PC or other digital processing engine.

The digital memory 17, 18 may receive data from sensors 10, 11. Each sensor 10, 11 may include or be associated with an analog to digital (A to D) converter 19, 20. The or each A to D converter 19, 20 and memory 17, 18 may be associated directly with sensors 10, 11 such as being located on the same PCB as sensors 10, 11 respectively. Alternatively sensors 10, 11 may output analog data to transmitters 13, 14 and one or more A to D converters may be associated with remote receiver 15 and/or digital processing engine 16. The one or more A to D converters may convert the analog data to a digital domain prior to storing the data in a digital memory such as a digital memory described above. In some embodiments digital processing engine 16 may process data in real time to provide biofeedback to subject 12 being monitored.

FIG. 2 shows a top-down cross-sectional view in the transversal plane of the left leg of subject 12 with sensor 10 placed on face 20 of tibia 21. The angle between face 20 on tibia 21 and the forward flexion plane is defined as $\Phi$. Angle $\Phi$ may be approximately 45 degrees for an average subject but may vary a few degrees up or down from the average value. Face 20 may provide a relatively stable platform for attachment of sensor 10. The frame of reference (B) for sensor 10 is therefore rotated relative to the frame of reference (C) of the mechanical axis of tibia 21 by the magnitude of angle $\Phi$. Flexion and lateral flexion are defined as rotations around axes $C_Y$ and $C_Z$ while gyroscope and accelerometer sensitivity axes of sensor 10 are aligned with axes $B_Y$ and $B_Z$.

Because measurements via sensor 10 are obtained in sensor reference frame B they must be converted to tibia reference frame C. The following equations may be used for this transformation:

$$Cy = By*\cos(\Phi) + Bz*\sin(\Phi) \quad (1)$$

$$Cz = By*\sin(\Phi) - Bz*\cos(\Phi) \quad (2)$$

wherein By, Bz denote y and z components in sensor reference frame B, Cy and Cz denote y and z components in tibia reference frame C, and $\Phi$ denotes the angle between sensor 10 on tibia 21 and the forward flexion plane.

Equations (1) and (2) above may be used to vector transform gyroscope signals $\{^B\omega_x, {}^B\omega_Y \text{ and } {}^B\omega_Z\}$ and optionally accelerometer signals $\{^B a_x, {}^B a_Y \text{ and } {}^B a_Z\}$ obtained via sensor 10 in sensor reference frame B, to gyroscope signals $\{^C\omega_x, {}^C\omega_Y \text{ and } {}^C\omega_Z\}$ and accelerometer signals $\{^C a_x, {}^C a_Y \text{ and } {}^C a_Z\}$ respectively in mechanical or tibia reference frame C.

Following vector transformation, the gyroscope signals $\{^C\omega_x, {}^C\omega_Y \text{ and } {}^C\omega_Z\}$ representing angular velocity may be integrated over a period of time t representing the duration of an activity such as squatting, hopping and/or running using the following equation to provide an integrated angular displacement ($\theta$):

$$\theta = \int_0^t \omega \cdot dt \quad (3)$$

The integrated signals e may be corrected for gyroscope drift errors caused by noise and/or other artefacts. Drift correction may be performed using a known angular reference provided by the accelerometer signals. The flexion angle ($\theta_Y$) may be corrected for drift at the start and at the end of a hop/squat using the flexion angle ($\beta_y$) obtained from the accelerometer signals using the following equation:

$$\beta_y = a \tan({}^c a_y / {}^c a_x) \quad (4)$$

The lateral flexion angle ($\theta_Z$) may be corrected for drift using lateral flexion angle ($\beta_z$) obtained from the accelerometer using the following equation:

$$\beta_z = a \tan({}^c a_z / {}^c a_x) \quad (5)$$

The twist angle ($\theta_X$) may be corrected with zero as there is no rotation around gravity measured by the accelerometer.

As a player flexes the knee, the degree of medio/lateral deviation is measured with respect to mechanical or tibia reference frame (C). However, this value is transformed with respect to the visual reference frame of the tester, also known as the frontal or viewer plane to provide more intuitive results.

It is possible for the leg to rotate around the x-axis when the player hops and lands. Hence, the visual impression of the lateral flexion will change if the rotation around the x-axis is not compensated. This effect is represented in equation 7, as it is used in the projection of the lateral flexion plane ($\theta_z$) with respect to the frontal plane.

FIG. 3 shows a projection of lateral flexion angle ($\theta_Z$) onto the frontal or viewer plane together with a twist update. To project lateral flexion angle ($\theta_Z$) onto the frontal or viewer plane the leg may considered to be a rigid rod with fixed joint on the ankle. The length of the rod may be normalized as 1. Angular displacement on the $\theta_X$ plane (caused by $\theta_Y$ and $\theta_Z$ only) may be determined by:

$$\theta_{x0} = a \tan(\sin(\theta_Z)/\tan(\theta_Y)) \quad (6)$$

Actual twist movement $\theta_{x0}$ may be added to angular displacement $\theta_X$ to determine resultant angular displacement $\theta_{xresultant}$:

$$\theta_{xresultant} = \theta_x + \theta_{x0} \quad (7)$$

One goal is to determine the terms A, B and C in order to calculate $\theta_{zAdjusted}$. For this, the projection of $\theta_Z$ on $\theta_X$ will result in A:

$$A = \sin(\theta_Z)/\sin(\theta_x 0)*\sin(\theta_x) \quad (8)$$

The projection of $\theta_X$ on $\theta_Y$ will determine B:

$$B = \sin(\theta_Z)/\sin(\theta_{x0})*\cos(\theta_x) \quad (9)$$

C is calculated assuming the length of the rod is 1:

$$C = \text{sqrt}(1 - B^2) \quad (10)$$

Finally, calculate a sin of A and C to obtain the drift adjusted $\theta_Z$ and projected onto the frontal plane as $\theta_{zAdjusted}$:

$$\theta_{ZAdjusted} = a \sin(A/C) \quad (11)$$

Figure 4:
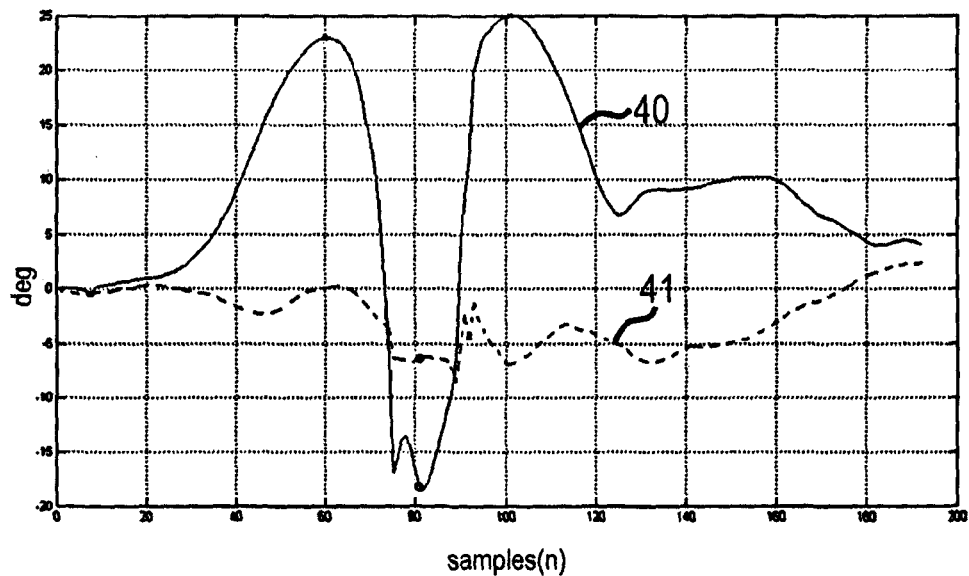
FIG. 4 shows test results for a first subject with little or no medio-lateral deviation.

FIG. 4 shows test results for a subject with normal angular deviation of the knee during a jump. In FIG. 4, curve 40 represents flexion angle ($\theta_Y$) in degrees plotted over the duration of the jump, while curve 41 represents lateral flexion angle ($\theta_Z$) in degrees plotted over the same duration of the jump. Curve 41 shows reduced medio-lateral deviation of flexion indicating negligible rotation around the y axis. Therefore the test indicates that this subject exhibits little or no medio-lateral deviation i.e. neither valgus nor varus.

Figure 5:
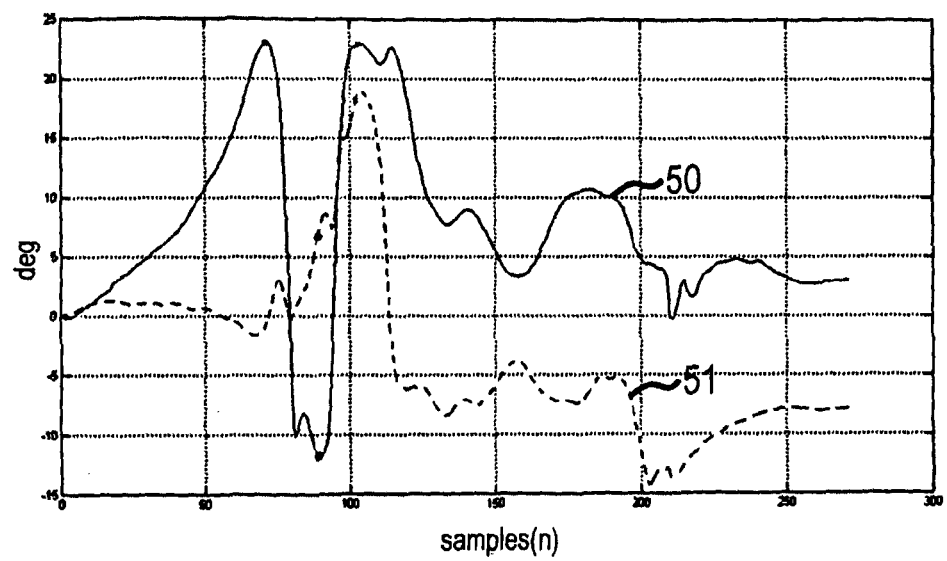
FIG. 5 shows test results for a second subject with Varus deviation.

FIG. 5 shows test results for another subject with significant angular deviation of the knee during a jump. In FIG. 5, curve 50 represents flexion angle ($\theta_Y$) in degrees plotted over the duration of the jump, while curve 51 represents lateral flexion angle ($\theta_Z$) in degrees plotted over the same duration of the jump. Curve 51 shows positive lateral deviation indicating approximately +18 degree rotation around the y axis. Therefore the test indicates that this subject exhibits Varus deviation i.e. the knee deviates outwards.

Figure 6:
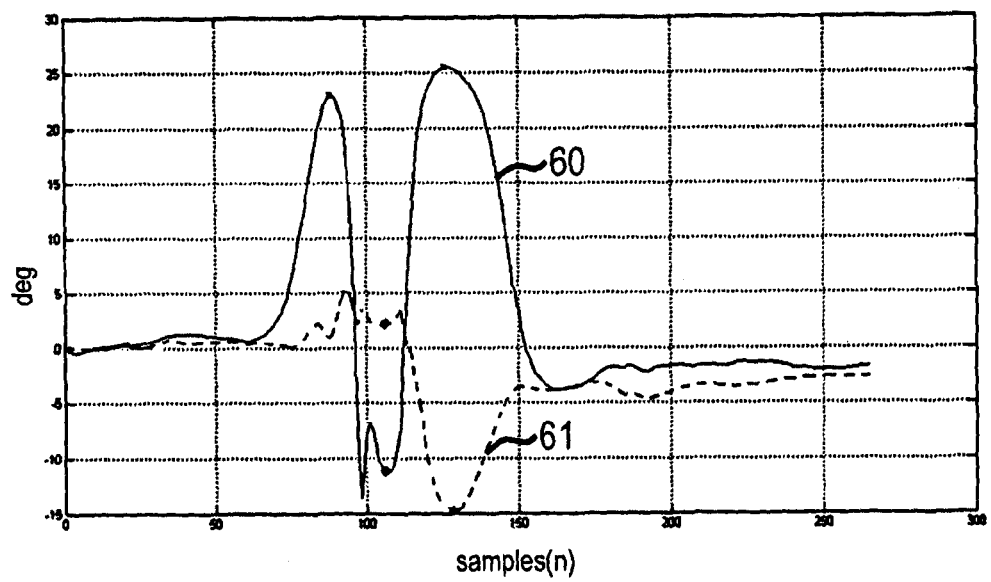
FIG. 6 shows test results for a third subject with Valgus deviation.

FIG. 6 shows test results for another subject with significant angular deviation of the knee during a jump. In FIG. 6, curve 60 represents flexion angle ($\theta_Y$) in degrees plotted over the duration of the jump, while curve 61 represents lateral flexion angle ($\theta_Z$) in degrees plotted over the same duration of the jump. Curve 61 shows negative lateral flexion angles indicating approximately −15 degree rotation around the y axis. Therefore the test indicates that this subject exhibits Valgus deviation i.e. the knee deviates inwards.

Finally, it is to be understood that various alterations, modifications and/or additions may be introduced into the constructions and arrangements of parts previously described without departing from the spirit or ambit of the invention.

The invention claimed is:

1. Apparatus for monitoring, measuring and/or estimating deviation of a body part of a vertebral mammal, said apparatus including:
   at least one sensor for measuring rotation of said body part relative to a first frame of reference and for providing data indicative of said rotation;
   a memory device adapted for storing said data; and
   a processor adapted for processing said data to evaluate a deviation of said body part that correlates to said data;
   wherein said processor is configured to execute an algorithm for evaluating said deviation of said body part, wherein said algorithm is adapted to:
     integrate said data over a period of time to provide an angular displacement ($\theta$);
     evaluate a twist component ($\theta_X$) of said angular displacement representing twist angle; and
     compensate said twist component ($\theta_X$) by adding an angular offset ($\theta_{x0}$) to said twist component ($\theta_X$).

2. Apparatus according to claim 1, wherein said algorithm is adapted to transform said data from said first frame of reference relative to a second frame of reference in which said body part performs a movement.

3. Apparatus according to claim 1, wherein said algorithm is adapted to evaluate a component ($\theta_Z$) of said angular displacement representing valgus or varus angle.

4. Apparatus according to claim 3, wherein said algorithm is adapted to project said lateral flexion component ($\theta_Z$) onto a frontal plane.

5. Apparatus according to claim 1, wherein said angular offset ($\theta_{x0}$) is caused by components ($\theta_Y$) and ($\theta_Z$) of said angular displacement and is determined by $\theta_{x0}=a\tan(\sin(\theta_Z)/\tan(\theta_Y))$.

6. Apparatus according to claim 1 wherein said at least one sensor includes a gyroscope.

7. Apparatus according to claim 1 wherein said at least one sensor is adapted for measuring rotation around one or more orthogonal axes.

8. Apparatus according to claim 1 wherein said at least one sensor is adapted for measuring acceleration of said body part relative to an inertial frame of reference and for providing data indicative of said acceleration.

9. Apparatus according to claim 8 wherein said at least one sensor is adapted for measuring acceleration along one or more orthogonal axes.

10. Apparatus according to claim 1 wherein said body part of said mammal includes legs and said apparatus is adapted to monitor rotation components associated with said legs.

11. Apparatus according to claim 10, wherein respective sensors are applied to the legs of said mammal.

12. Apparatus according to claim 1 wherein said at least one sensor includes an analog to digital (A to D) converter for converting analog data to a digital domain.

13. Apparatus according to claim 12 wherein said A to D converter is configured to convert an analog output from said at least one sensor to said data prior to storing said data.

14. Apparatus according to claim 1 adapted for providing feedback of said deviation to a subject being monitored.

15. A method of monitoring, measuring and/or estimating deviation of a body part of a vertebral mammal, said method including:
using at least one sensor to measure rotation of said body part relative to a first frame of reference and for providing data indicative of said rotation;
storing said data in a memory device; and
processing said data by a processor to evaluate a deviation of said body part that correlates to said data;
wherein said processor is configured to execute an algorithm for evaluating said deviation of said body part, wherein said algorithm is adapted to:
integrate said data over a period of time to provide an angular displacement ($\theta$);
evaluate a twist component ($\theta_X$) of said angular displacement representing twist angle; and
compensate said twist component ($\theta_X$) by adding an angular offset ($\theta_{x0}$) to said twist component ($\theta_X$).

16. A method according to claim 15, wherein said algorithm is adapted to transform said data from said first frame of reference relative to a second frame of reference in which said body part performs a movement.

17. A method according to claim 15, wherein said algorithm is adapted to evaluate a component ($\theta_Z$) of said angular displacement representing valgus or varus angle.

18. A method according to claim 17, wherein said algorithm is adapted to project said lateral flexion component ($\theta_Z$) onto a frontal plane.

19. A method according to claim 15, wherein said angular offset ($\theta_{x0}$) is caused by components ($\theta_Y$) and ($\theta_Z$) of said angular displacement and is determined by $\theta_{x0}=a\tan(\sin(\theta_Z)/\tan(\theta_Y))$.

20. A method according to claim 15 wherein said at least one sensor includes a gyroscope.

21. A method according to claim 15 wherein said at least one sensor is adapted for measuring rotation around one or more orthogonal axes.

22. A method according to claim 15, wherein said at least one sensor is adapted for measuring acceleration of said body part relative to an inertial frame of reference and for providing data indicative of said acceleration.

23. A method according to claim 22 wherein said at least one sensor is adapted for measuring acceleration along one or more orthogonal axes.

24. A method according to claim 15 wherein said body part of said mammal includes legs and said method includes monitoring rotation components associated with said legs.

25. A method according to claim 24, wherein respective sensors are applied to the legs of said mammal.

26. A method according to claim 15, wherein said at least one sensor includes an analog to digital (A to D) converter for converting analog data to a digital domain.

27. A method according to claim 26, wherein said A to D converter is configured to convert an analog output from said at least one sensor to said data prior to storing said data.

28. A method according to claim 15 including providing feedback of said deviation to a subject being monitored.

* * * * *